US010307217B2

(12) United States Patent
Sparkuhl

(10) Patent No.: US 10,307,217 B2
(45) Date of Patent: Jun. 4, 2019

(54) FACIAL PROTECTION AND THERMOREGULATION FOR PATIENTS UNDERGOING SURGERY

(71) Applicant: Michael Dimitri Sparkuhl, Santa Paula, CA (US)

(72) Inventor: Michael Dimitri Sparkuhl, Santa Paula, CA (US)

(73) Assignee: DOMA PATIENT SAFETY PRODUCTS, LLC, Santa Paula, CA (US)

( * ) Notice: Subject to any disclaimer, the term of this patent is extended or adjusted under 35 U.S.C. 154(b) by 663 days.

(21) Appl. No.: 14/737,880

(22) Filed: Jun. 12, 2015

(65) Prior Publication Data

US 2015/0272687 A1    Oct. 1, 2015

Related U.S. Application Data

(63) Continuation-in-part of application No. 14/278,276, filed on May 15, 2014, now abandoned.

(Continued)

(51) Int. Cl.
*A41D 13/11* (2006.01)
*A61B 90/00* (2016.01)
(Continued)

(52) U.S. Cl.
CPC ............. *A61B 90/04* (2016.02); *A61M 16/06* (2013.01); *A61M 16/0627* (2014.02);
(Continued)

(58) Field of Classification Search
CPC ............. A61M 16/06; A61M 16/0605; A61M 16/0627; A61M 16/0666; A61M 16/0633; A61M 2016/0661; A61M 16/0616; A61M 16/0622; A62B 18/02; A62B 18/04; A62B 18/06; A62B 18/08; A62B 18/084;
(Continued)

(56) References Cited

U.S. PATENT DOCUMENTS 4,022,200 A * 5/1977 Jonson ................. A61M 16/06
                                                    128/205.25
4,328,797 A * 5/1982 Rollins, III ........... A61M 16/06
                                                    128/202.15

(Continued)

*Primary Examiner* — Kari K Rodriquez
*Assistant Examiner* — Camtu T Nguyen
(74) *Attorney, Agent, or Firm* — M. J. Ram and Associates

(57) ABSTRACT

A mask suitable for protecting the face of a patient during surgery comprises a transparent plastic shield which includes a transverse cutout that provides access to the nose and mouth, and a vertical gap which runs from the cutout to the shield's perimeter. Padding affixed to the perimeter of the shield's underside provides a cushion between the shield and face. The padding is preferably arranged such that the mask can be installed or removed without dislodging tubing inserted into the patient's nose or mouth via the transverse cutout. An attachment mechanism secures the shield to the face. A warming hood may be coupled to the protective mask. The hood preferably comprises outer and inner layers, with an access point at which air can be introduced between the layers; perforations on the inner layer permit warm air to be dispersed onto the patient.

43 Claims, 5 Drawing Sheets

Related U.S. Application Data

(60) Provisional application No. 61/824,744, filed on May 17, 2013.

(51) Int. Cl.
*A61M 16/06* (2006.01)
*A61M 16/10* (2006.01)
*A61M 16/04* (2006.01)

(52) U.S. Cl.
CPC ... *A61M 16/1075* (2013.01); *A61B 2090/049* (2016.02); *A61B 2090/0436* (2016.02); *A61B 2090/0463* (2016.02); *A61M 16/04* (2013.01); *A61M 16/0683* (2013.01); *A61M 2205/362* (2013.01)

(58) Field of Classification Search
CPC ........... A41D 13/11; A41D 13/1107; A41D 13/1138; A41D 13/1146; A41D 13/1153; A41D 13/1161; A41D 13/1184; A41D 13/1215; A41D 13/1218; A61G 13/1215; A61B 46/23; A61B 2046/234; A42B 3/18; A42B 3/22; A61F 9/06; A61F 9/068; A61F 9/025; A61F 9/027; A61F 9/028; A61F 9/029; A61F 2009/021

USPC ........................................................ 128/857

See application file for complete search history.

(56) References Cited

U.S. PATENT DOCUMENTS

| | | | | |
|---|---|---|---|---|
| 4,470,413 | A * | 9/1984 | Warncke | A62B 18/084 128/201.18 |
| 6,112,333 | A * | 9/2000 | Mazzei | A61G 13/12 128/857 |
| 7,296,570 | B2 * | 11/2007 | Hutchinson | A61F 7/02 128/201.26 |
| 2008/0110463 | A1 * | 5/2008 | Hajgato | A61M 16/06 128/205.25 |

* cited by examiner

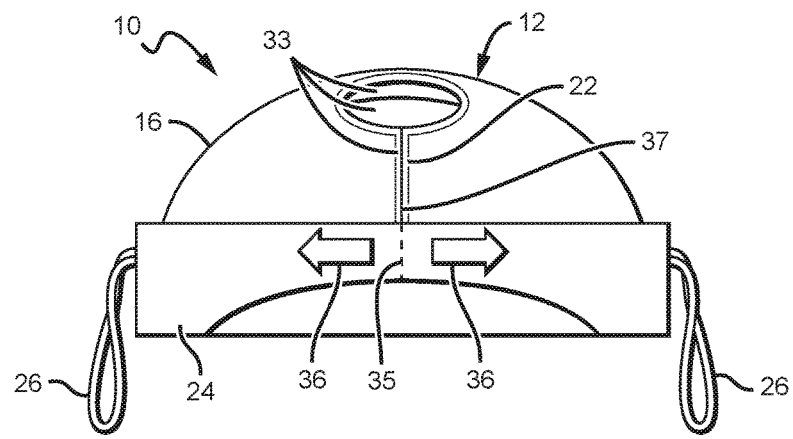
FIG. 1d
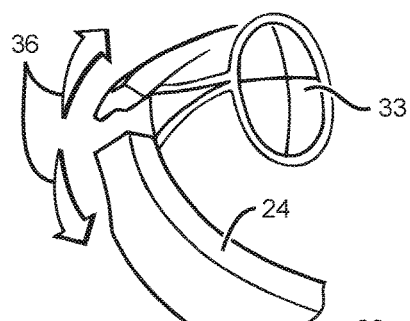
FIG. 1e
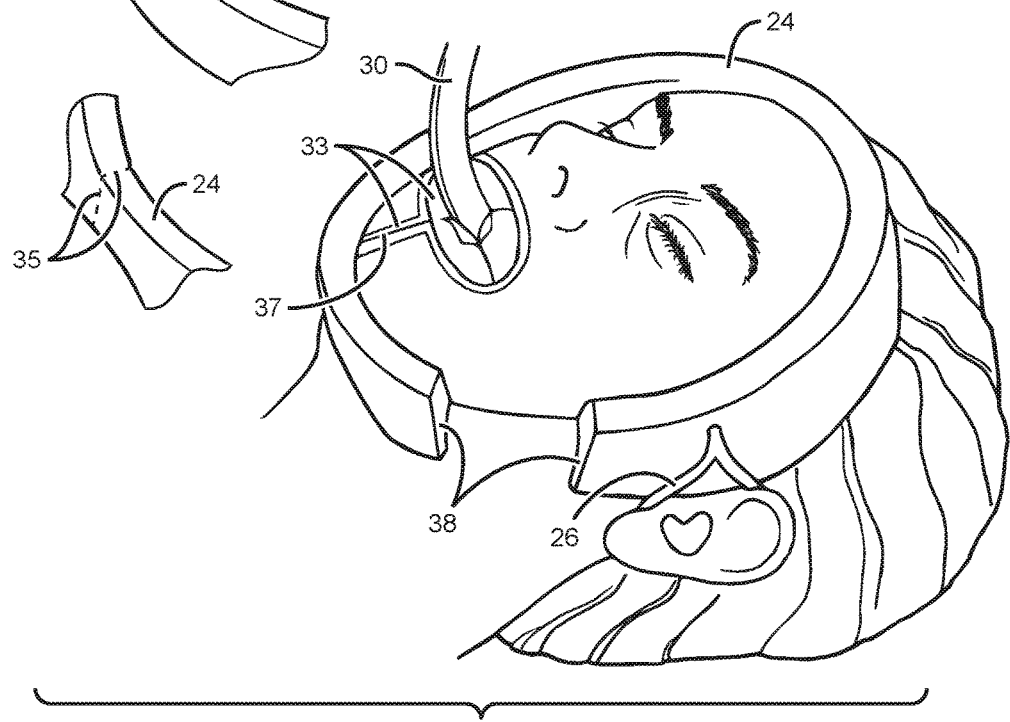

FACIAL PROTECTION AND THERMOREGULATION FOR PATIENTS UNDERGOING SURGERY

RELATED APPLICATIONS

This application is a continuation-in-part of U.S. application Ser. No. 14/278,276 filed on May 15, 2014, which claimed the benefit of provisional patent application No. 61/824,744 to Michael Dimitri Sparkuhl, filed May 17, 2013.

BACKGROUND OF THE INVENTION

Field of the Invention

The present invention relates generally to facial protection and thermoregulation for patients undergoing surgery.

Description of the Related Art

There is a growing interest in the safety of patients undergoing surgery, to avoid errors, injuries, and complications. Because many adverse events are preventable, the Joint Commission of Hospitals, the major hospital certifying agency for Medicare and CMS, and the World Health Organization, have devoted considerable resources to educating and monitoring health care professionals nationally and internationally in matters of patient safety and the prevention of surgery errors, injuries, and complications.

There are generally accepted and standardized approaches to patient positioning, and the use of padding, restraints, straps, bolsters, and various support mechanisms to prevent injuries. Methods of preventing injuries to the face during surgery vary depending on patient positioning. For example, there is considerable discussion of facial protection in anesthesia literature, which discusses patients in the face down or prone position when undergoing spinal surgery or other procedures requiring that position. The emphasis here is on eye, nose, and lip protection and airway access, with eye and airway having the highest priority and being at the greatest risk. There are a few products available to help protect against injuries in this position, such as contoured foam rubber pads, modified head gear pads, adhesive eye goggles, and table mirrors which allow an anesthesiologist to see a patient's face in the prone position. Some of these methods also apply to patients placed in the decubitus position (patient lying on right or left side).

The majority of operations, however, are performed with the patient in the supine or face up position. In this position the face is exposed and unprotected, rendering it vulnerable to falling or dropped objects, instruments inadvertently striking the face, eyes or teeth, unanticipated drips of chemicals, body fluids, prep-solutions, etc. Eye and tooth injuries are the most common facial injuries in the operating room, occurring in about 1:1000 cases. Considering that about 24-44 million operations are performed annually in the USA, there are many injuries occurring which probably go unreported.

Despite these concerns, facial protection of a patient in the supine position is not standardized; it is typically left up to the anesthesiologist to best determine how to protect the face from mechanical or fluid-related injury. Conventional protection efforts may involve, for example, periodic visual inspection so as to keep the surgical drapes, as well as the surgeon's hands, arms, instruments and instrument trays away from the patient's face. Folded sheets, towels, or unsecured foam rubber pads may also be placed over the face. However, using these approaches, an injury might occur while the anesthesiologist is otherwise occupied and not constantly watching the patient's face. In addition, access to the face required by the anesthesiologist may be compromised by the various non-transparent items placed on the face; those items might also provide inadequate facial protection. There are no known devices specifically designed for facial protection under general anesthesia when the patient is in a supine position.

Another problem that can arise during a surgical procedure is inadvertent intraoperative hypothermia, due to exposure of the head and face with concomitant heat loss. This is known to be dangerous for the patient and can lead to surgical complications. It is known that the head may lose as much as 30% of body heat under stress and anesthesia. Forced air heating units are commonly used for the extremities and torso, but none are independently available and dedicated to the head & neck area.

SUMMARY OF THE INVENTION

A protective mask suitable for protecting the face of a patient during surgery is presented, which provides for predictable, standardized facial protection of patients under general anesthesia in the supine position. A warming hood is also presented which prevents heat loss from the head, neck, and shoulders, and may also be used to actively warm these areas to prevent inadvertent intraoperative hypothermia.

The present protective mask comprises a transparent plastic shield sized and shaped to protect the face of a patient when the mask is installed. The shield has a convex topside and an underside, and includes a transverse cutout through the shield which provides access to the patient's nose and mouth, and a vertical gap which runs from the transverse cutout to the lower perimeter of the shield. The transverse cutout is sized to permit the passage of airway (endotracheal (ET) or laryngeal mask airway (LMA)) and enteric (nasogastric/orogastric) tubing to the patient's mouth and nose. A membrane may be placed over or under the transverse cutout, which is slit to permit the passage of tubing through the mask; the membrane may also be over the vertical gap. The membrane provides at least a partial seal around the tubing that passes through the cutout, as well as to stabilize the tubing and to prevent at least some operative debris and/or fluids from reaching the patient's mouth by flowing around the tubing.

Padding, preferably latex-free, is affixed to the perimeter of the underside of the shield which contacts the patient's face and provides a cushion between the shield and the face when the mask is installed. The padding is arranged to allow the patient's face to remain substantially visible through the shield when the protective mask is installed. The padding is preferably arranged such that the mask can be installed on or removed from the face of the patient without dislodging tubing inserted into the patient's nose or mouth. This can be accomplished by scoring or perforating the padding in the area of the vertical gap, or by pre-cutting the padding so that it is discontinuous. An attachment mechanism secures the shield and padding to the patient's face.

A warming hood may also be employed; the hood is arranged to be coupled to the protective mask and covers the head, neck and shoulders when so coupled. The hood preferably comprises a blanket having an outer layer and an inner layer, with the outer and inner layers heat sealed to each other at their respective perimeters. The blanket has at least one access point at which air can be introduced between the outer and inner layers; the inner layer comprises a plurality of micro-perforations through which air introduced via the access points is dispersed onto the patient.

These and other features, aspects, and advantages of the present invention will become better understood with reference to the following description and claims.

BRIEF DESCRIPTION OF THE DRAWINGS

FIG. 1d is a side elevation view of another possible embodiment of a protective mask protective mask per the present invention.

FIG. 1e is a perspective view and two inset views of another possible embodiment of a protective mask protective mask per the present invention.

DETAILED DESCRIPTION OF THE INVENTION

Figure 1A:
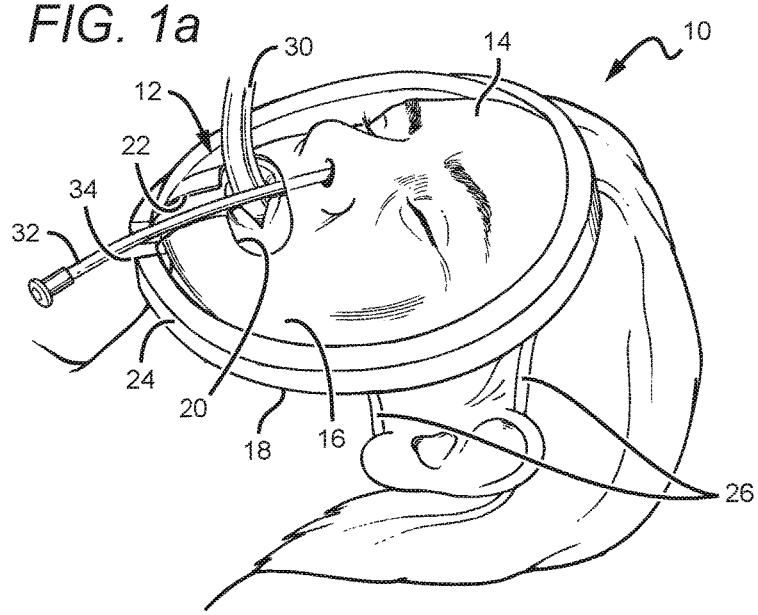
FIGS. 1a and 1b are perspective views of a protective mask per the present invention.
Figure 1B:
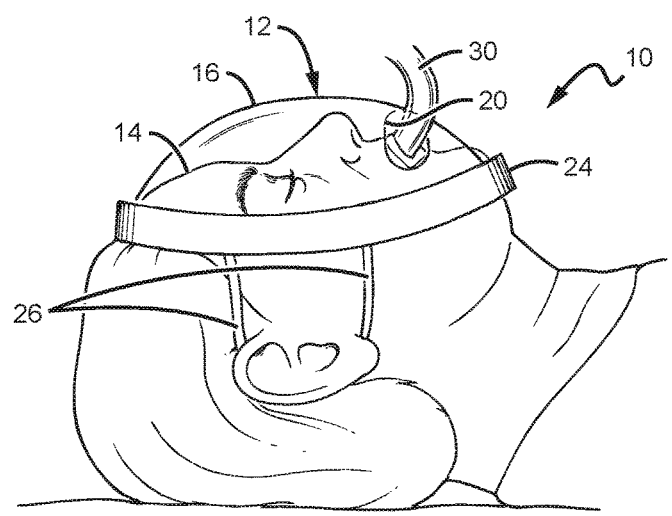

A protective mask, suitable for protecting the face of a patient during surgery, is shown in FIGS. 1a and 1b (perspective views) and 1c (front elevation view). The mask 10 comprises a transparent plastic shield 12 sized and shaped to protect the face of a patient 14 when the mask is installed on the patient's face. Shield 12 has a convex topside 16 and an underside 18. The shield includes a transverse cutout 20 through the shield which provides access to the patient's nose and mouth, and a vertical gap 22 which runs from the transverse cutout to the perimeter of the shield. The protective mask also includes padding 24 affixed to the perimeter of the underside of shield 12, which contacts the patient's face and provides a cushion between the shield and face when the mask is installed on the patient's head. Padding 24 is arranged to allow the patient's face to remain substantially visible through the shield when the mask is installed on the patient's face. An attachment mechanism 26 secures shield 12 and padding 24 to the face of patient 14.

Transverse cutout 20 is sized to permit the passage of tubing to the nose and mouth; this may include, for example, at least two of an ET tube 30, a LMA tube (not shown), and a nasogastric or orogastric tube 32. Mask 10 is arranged such that, when installed on the face of a patient, transverse cutout 20 is over the patient's mouth and vertical gap 22 runs from the transverse cutout to the perimeter of the shield over the patient's chin, such that the transverse cutout and vertical gap form a T-shaped opening through the shield.

As shown in FIGS. 1d and 1e, the present mask may also include a membrane 33 over or under the transverse cutout 20; the membrane may also be over vertical gap 22. The membrane is slit to permit the passage of tubing through the mask. Membrane 33 serves to provide at least a partial seal around the tubing that passes through the cutout, as well as to stabilize the tubing and to prevent at least some operative debris and/or fluids from reaching the patient's mouth by flowing around the tubing. Membrane 33 could be affixed to either the topside 16 or underside of shield 12.

Padding 24 may include a discontinuity 34 in the area of vertical gap 22. Plastic shield 12, transverse cutout 20, vertical gap 22 and discontinuous padding 24 are arranged such that the protective mask can be installed on or removed from the face of patient 14 without dislodging tubing (30, 32) inserted into the patient's nose or mouth. Transverse cutout 20 is suitably approximately 4 inches wide by 1 inch high and vertical gap 22 is suitably approximately 0.75 inch wide by 3 inches high, though both of these may be differently sized as needed for a given application. The vertical gap allows unencumbered rapid placement, positioning and removal of the mask with no tube disturbance or disconnect, while the transverse cutout allows further tube positioning from side to side, permitting flexibility of tube extension placement from the anesthesia machine.

Figure 1C:
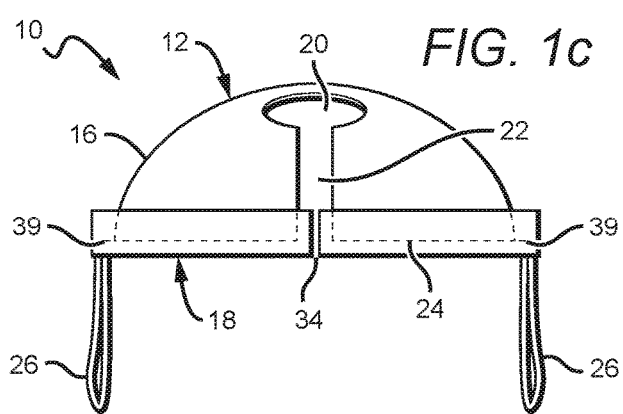
FIG. 1c is a side elevation view of a protective mask per the present invention.

Though padding 24 is shown as including a discontinuity 34 in FIGS. 1a-1c, this is not essential. For example, padding 24 may simply be continuous. Another alternative is that the padding be scored or perforated in the area of vertical gap 22. This is illustrated in FIGS. 1d and 1e. Here, the padding includes a scored or perforated area 35 that enables the padding to be continuous unless it is intentionally pulled in opposite directions on either side of area 35, in which case the padding separates along the scoring and becomes discontinuous. The inset drawings in FIG. 1e illustrate the padding pre- and post-separation. Membrane 33 is preferably also slit 37, such that it separates along with the padding when the padding is intentionally pulled in opposite directions.

Instead of being scored or perforated, padding 24 might alternatively be pre-cut in the area of vertical gap 22, with the padding on one side of the cut kept in contact with the padding on the other side of the cut by some securing means until intentionally pulled in opposite directions. For example, the padding on either side of the cut could be held together with glue, tape, a hook and loop system, or Velcro. Another possibility is to affix a single hook to the padding on one side of the cut and a single loop, preferably elastic, on the other side of the cut; the padding is held closed when the hook is engaged with the loop, but can be separated by either disengaging the hook from the loop, or by forcing the two sides apart.

Rather than having a rectangular cross-section, the underside of padding 24 might be contoured to better fit against the face. This is illustrated in FIG. 1e, in which a segment of padding 24 is not shown so that the contoured underside 38 of the padding can be seen.

Shield 12 is preferably a molded plastic shield made from FDA-approved medical grade plastic. In addition to protecting the face from injury due to falling objects or fluids, the shield may be fabricated with impregnated or film barriers to protect the face—including the eyes—from ultraviolet rays, X-rays, and/or laser light. The shield is preferably fabricated by vacuforming plastic over a mold, with the tube cutouts made with a computer controlled cutter or die cutting before die-cutting the periphery of extraneous plastic to free the final transparent mask.

Padding 24 is preferably FDA-approved, hypoallergenic medical grade foam padding. The padding is preferably pre-slit prior to its being installed on shield 12 to provide discontinuity 34 in the area of vertical gap 22. Note that padding 24 may be implemented with materials other than foam padding. For example, the padding may be a flexible plastic bladder, preferably latex-free containing air or a conformable material, or comprise disposable cotton padding.

Attachment mechanism 26 is preferably affixed to plastic shield 12, though attachment to padding 24 is also contemplated. Attachment mechanism 26 can take a number of different forms; a preferred attachment mechanism comprises elastic ear loop retainers as illustrated in FIGS. 1a-1c. Alternatives include a behind-head elastic strap, a behind-head hook-and-loop strap, or a four point head strap harness typically used for anesthesia masks.

Another possible attachment mechanism is a low tack skin adhesive between the patient's face and the surface of padding 24 which contacts the face. A preferred adhesive is an electron beam cure synthetic polymer or other low tack skin adhesive.

Padding 24 could be attached to the shield in many different ways. In a preferred embodiment, plastic shield 12 includes a flange 39 which extends circumferentially approximately ¼" from the perimeter of the shield (shown in FIG. 1c), so that it substantially forms a right angle with the topside of the shield. Padding 24 may then comprise first and second pieces of foam padding which are sandwiched on either side of flange 39 and affixed to the flange with double-sided sticky tape or other easily applied non-toxic adhesive. The ends of attachment mechanism 26 which are affixed to plastic shield 12 would typically pass through the sandwiched foam padding enroute to the shield.

Padding 24 might alternatively comprise just a single piece of foam padding which is affixed only to the underside of shield 12 or flange 39. In this case, the outer edge of shield 12 would typically be exposed. A bead can be placed around the outer lip of shield 12 to soften the edge. Attachment mechanism 26 could be attached to shield 12 with, for example, glue.

When attachment mechanism 26 comprises elastic ear loop retainers, the retainers are preferably pre-cut into thin elastic loops of an appropriate length, and attached with heat sealing or non-toxic glue to the right and left sides of plastic shield 12 to match generally accepted adult ear level.

Another possible means of attaching padding 24 to shield 12 requires inserting the shield into a circumferential slit cut into the padding; assuming foam padding, the slit might be created using, for example, a foam cutting knife set up in a jig. Once inserted into the slit, the shield could be held in place with a non-toxic rapid-drying adhesive, or heat sealed. The padding might be die-cut, or molded into the desired shape using injection molding techniques.

A protective mask as described herein could be provided in various sizes, to provide a proper 'fit' for various face sizes—i.e., having a perimeter large enough to protect the entire face without extending significantly beyond the face. For example, the mask could be provided in small, medium and large sizes, and/or in pediatric and adult sizes.

Figure 1F:
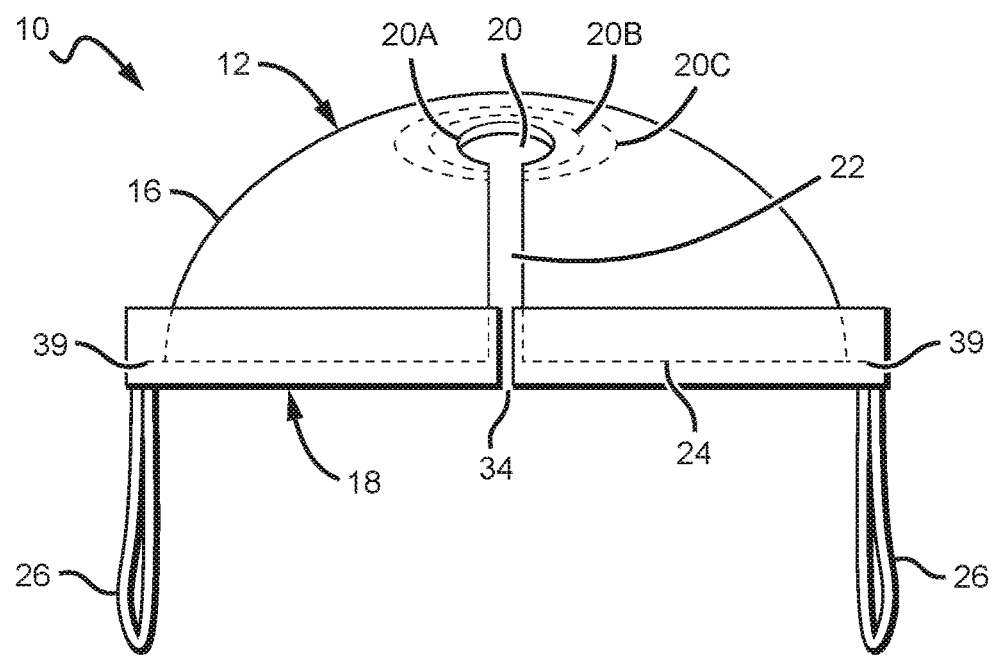
FIG. 1f is a side elevation view of a protective mask per the present invention, which illustrates that the present mask can have different transverse cutout sizes.

Masks might also be made available with a variety of transverse cutout sizes; this is illustrated in FIG. 1f which shows three potential sizes (20a, 20b, 20c) for transverse cutout 20. For example, a mask could be arranged such that the transverse cutout has the smallest possible size capable of accommodating a known tube or combination of tubes. For example, transverse cutout 20 might be sized to accommodate only a small ET tube, or to accommodate a large LMA tube. Choosing a mask with the smallest possible transverse cutout size for a particular patient serves to minimize the exposure of the face. Typical ET tubes have outside diameters (ODs) that range in size from 3.4 mm (neonates) to 13 mm (adults), while typical LMA tubes have ODs that range in size from 8 mm (1#) to 16.8 mm (6#). Note that in addition to an ET and/or LMA, a mask's transverse cutout would also typically need to allow the passage of a nasogastric tube.

Figure 2:
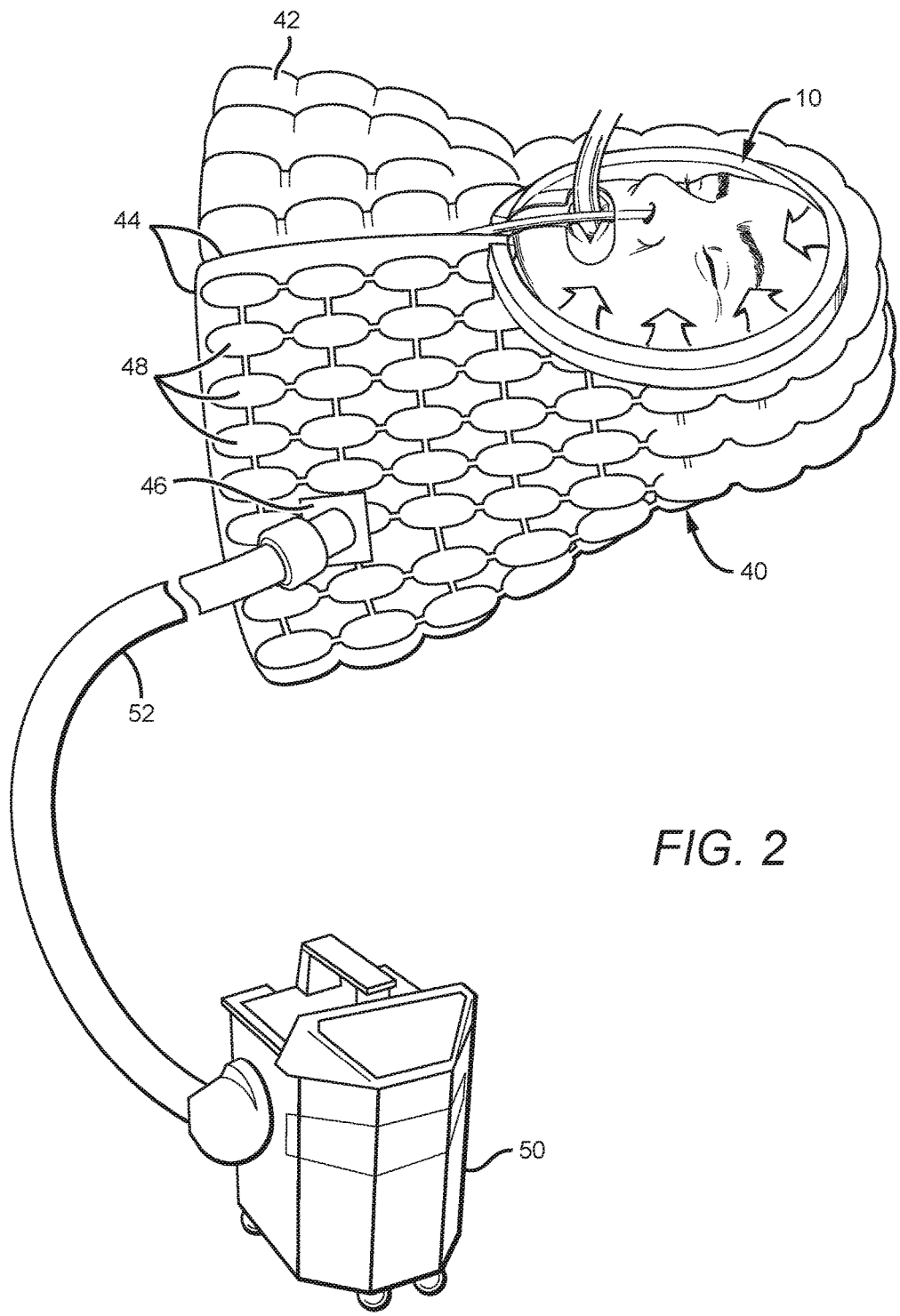
FIG. 2 is a perspective view of the present protective mask, used in combination with a warming hood per the present invention.

A warming hood can be coupled to the protective mask, which covers the head, neck and shoulders when so coupled. An exemplary embodiment is shown in FIG. 2, with warming hood 40 coupled to a protective mask 10 as described above. The hood 40 preferably comprises a blanket, which is preferably coupled to mask 10 by having an edge of the blanket attached to flange 39 (shown in FIG. 1c). The blanket edge is suitably attached to approximately 75% of the flange, with the bottom (chin end) of the mask left open so that there is room to place the mask/hood over the face and head, much like a scarf is placed over one's head and then draped across the neck. In practice, the loose edges of the blanket at the neck and shoulder level would then be gathered and held together in front of the patient with self-sticking tape, hook-and-loop attachment, plastic snap, or other simple mechanism to provide maximum envelopment of the head, neck, shoulders, and upper chest.

The warming hood could be implemented in many different ways. In a preferred implementation, the warming hood's blanket has an outer layer and an inner layer (outer layer 42 shown), with the outer and inner layers heat sealed to each other at their respective perimeters 44. The blanket has at least one access point 46 at which air can be introduced into the blanket between the outer and inner layers; two access points are preferred, located on the right and left side of the patient when the blanket is draped over the head and shoulders, to enable the anesthesiologist to make connection to the hood on whichever side is best for a given operative situation. The inner layer comprises a plurality of micro-perforations (not shown) through which air introduced via the access points is dispersed onto the patient. The outer and inner layers of the blanket are preferably further heat sealed to each other at a plurality of points within the perimeter of said blanket, to form a plurality of linked chambers 48 through which air introduced via the access points is distributed around the interior of the blanket. The outer and inner layers of the warming hood's blanket are suitably thin Mylar sheets in a rectangular configuration of approximately 16×45 inches, though the hood might be made from different materials. For example, one or both layers could be clear medical-grade plastic, or clear Mylar on the 'up' side and micro-perforated paper on the 'down' (patient) side.

A warming hood as described above could be used with existing Operating Room warm air generators 50 or torso warming devices which force warmed air to the hood via a hose or hoses 52; alternatively, the hood could be provided as a stand-alone device. In this way, the warming hood acts to prevent inadvertent intraoperative hypothermia by heat retention, and to help maintain normal core body temperature.

Figure 3:
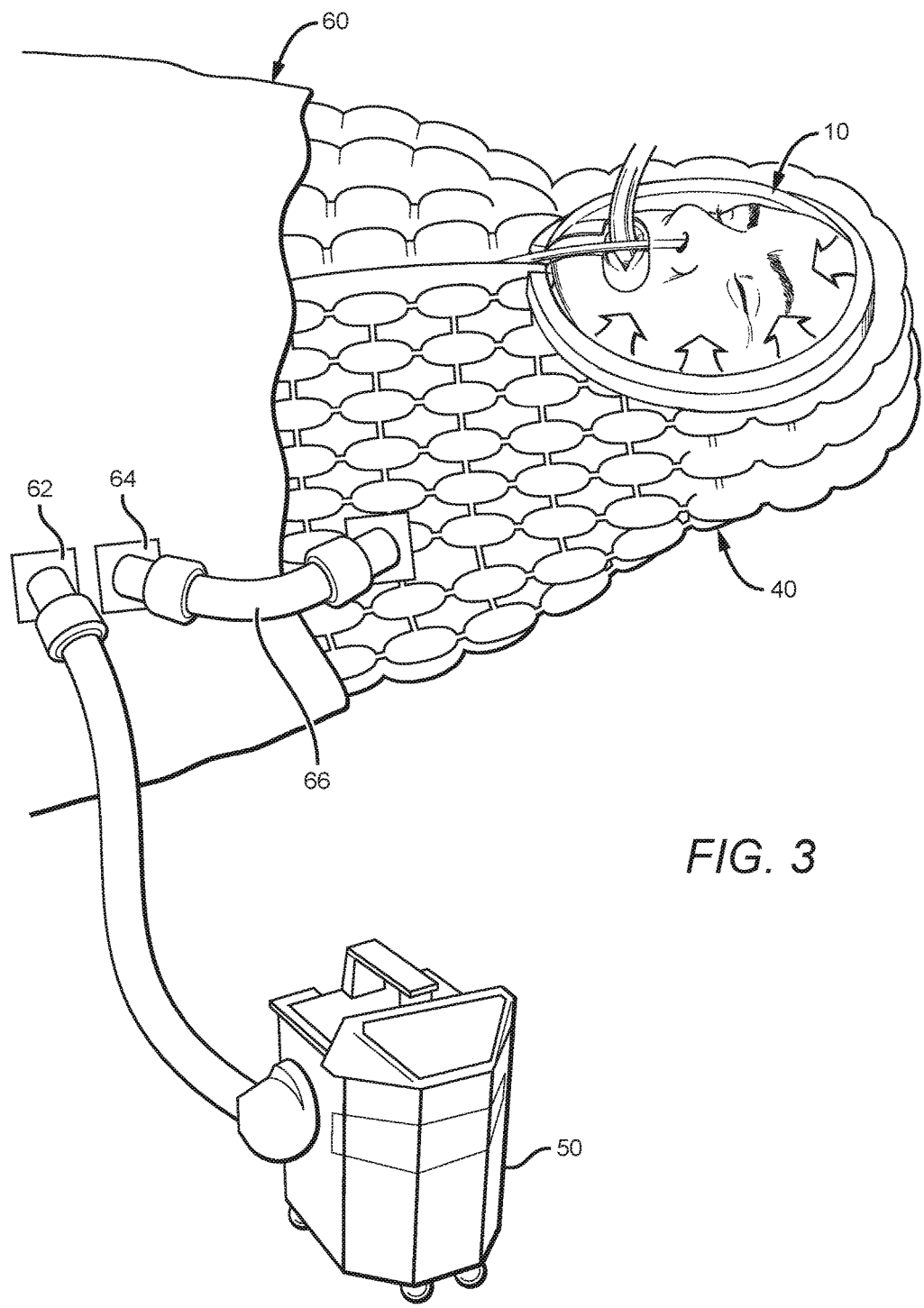
FIG. 3 is a perspective view of the present protective mask, used in combination with a warming hood and a thermal blanket per the present invention.

As shown in FIG. 3, a warming hood 40 as described above could also be used with an existing thermal blanket 60, with the warming hood used to warm the head and the existing blanket used to warm portions of the patient's body other than the head. The warming hood and thermal blanket might be arranged to be coupled together such that warm air introduced into thermal blanket 60 via an access port 62 may pass out of a supplementary access point 64 and flow into the warming hood via one of its access points (46). This coupling can be accomplished by means of a tube 66 connecting the two access points. Alternatively, the hood 40 and thermal blanket 60 could be arranged with their access points oriented in apposition to one another (not shown), creating a common channel for air flow from one to the other. In such a configuration, the warm air from the thermal blanket provides warm air to the hood, eliminating the need for an independent heat generator for the hood.

The present protective mask is preferably intended for a single use. The mask, or components thereof, could be made reusable if a means of sterilizing the components being reused were provided. For example, a protective mask might be provided for which padding 24 is intended to be single-use, but plastic shield 12 is intended to be reused; this would require that a means of sterilizing the plastic shield between uses be provided, along with a means of attaching new padding.

The present protective mask provides a standardized approach to patient facial protection, rather than relying on whatever might be randomly available to an anesthesiologist in the Operating Room. It eliminates surgeon-anesthesiologist confusion regarding facial protection, and provides for predictable, standardized facial protection of patients under general anesthesia in the supine position.

The mask can be advantageously employed wherever facial protection and core body temperature are important, such as low environmental temperature situations, low temperature work environments, search and rescue missions, and outdoor winter activities. The warming hood and blanket can also serve as a "space blanket", to insulate the individual and reflect heat back to the upper body. In addition to providing facial protection, the present mask can serve as temporary goggles, and aid with heat retention during transport.

The embodiments of the invention described herein are exemplary and numerous modifications, variations and rearrangements can be readily envisioned to achieve substantially equivalent results, all of which are intended to be embraced within the spirit and scope of the invention as defined in the appended claims.

I claim:

1. A protective mask suitable for protecting the face of a patient during surgery, comprising:
   a molded transparent plastic shield adapted to protect the face of a patient, including the patient's eyes, when said protective mask is installed on the face of said patient, said molded transparent plastic shield having a convex topside and an underside and including:
      a transverse cutout through said molded transparent plastic shield capable of providing access to the patient's nose and mouth and arranged to be over the patient's mouth when said protective mask is installed on said patient's face; and
      a continuous, pre-cut vertical gap in said molded transparent plastic shield which runs from said transverse cutout to the lower perimeter of said mold transparent plastic shield;
   padding affixed to the perimeter of the underside of said molded transparent plastic shield adapted to contact said patient's face and provides a cushion between said molded transparent plastic shield and said face when said protective mask is installed on the face of said patient, said padding arranged to allow said patient's face to remain substantially visible through said molded transparent plastic shield when said protective mask is installed on the face of said patient; and
   an attachment mechanism adapted to secure said protective mask to the face of said patient.

2. The mask of claim 1, wherein said padding is discontinuous in the area of said continuous, pre-cut vertical gap.

3. The mask of claim 1, wherein said padding is perforated or scored in the area of said continuous, pre-cut vertical gap.

4. The mask of claim 1, wherein said padding is pre-cut in the area of said continuous, pre-cut vertical gap, with the padding on one side of the cut kept in contact with the padding on the other side of the cut by a securing means.

5. The mask of claim 4, wherein said securing means comprises glue, tape, a hook and loop system, or Velcro.

6. The mask of claim 1, wherein said transverse cutout is sized to permit passage of at least two of an endotracheal tube, a laryngeal mask airway tube, and a nasogastric or orogastric tube.

7. The mask of claim 6, wherein said protective mask is provided with transverse cutouts of various sizes.

8. The mask of claim 6, wherein said protective mask is arranged such that the transverse cutout has the smallest possible size capable of accommodating a known tube or combination of tubes so as to minimize exposure of the face.

9. The mask of claim 1, further comprising a membrane over said transverse cutout, said membrane slit to permit the passage of tubing through said protective mask while providing a partial seal around said tubing and preventing at least some operative debris and/or fluids from reaching the patient's mouth by flowing around said tubing.

10. The mask of claim 9, wherein said membrane is affixed to either the topside or underside of said mold transparent plastic shield.

11. The mask of claim 9, wherein said membrane is also over said continuous, pre-cut vertical gap.

12. The mask of claim 1, wherein said protective mask is arranged such that, when installed on the face of said patient, said transverse cutout is adapted to be over said patient's mouth and said continuous, pre-cut vertical gap runs from said transverse cutout to the perimeter of said molded transparent plastic shield over said patient's chin, such that said transverse cutout and said continuous, pre-cut vertical gap form a T-shaped opening through said molded transparent plastic shield.

13. The mask of claim 1, wherein said molded transparent plastic shield, said transverse cutout, said continuous, pre-cut vertical gap and said padding are arranged such that said protective mask can be installed on or removed from the face of said patient without dislodging tubing inserted into said patient's nose or mouth.

14. The mask of claim 1, wherein said mold transparent plastic shield is made from FDA-approved medical grade plastic.

15. The mask of claim 1, wherein said mold transparent plastic shield is fabricated with impregnated or film barriers to protect said face, including the eyes, from ultraviolet rays, X-rays, and/or laser light.

16. The mask of claim 1, wherein said padding is pre-cut to provide said discontinuity in the area of said continuous, pre-cut vertical gap.

17. The mask of claim 1, wherein said padding is FDA-approved, latex-free hypoallergenic medical grade foam padding.

18. The mask of claim 1, wherein said padding is a latex-free flexible plastic bladder containing air or a conformable material.

19. The mask of claim 1, wherein said padding comprises disposable cotton padding.

20. The mask of claim 1, wherein said protective mask is intended for a single use.

21. The mask of claim 1, wherein said attachment mechanism is affixed to said plastic shield.

22. The mask of claim 1, wherein said attachment mechanism comprises elastic ear loop retainers.

23. The mask of claim 1, wherein said attachment mechanism comprises a behind-head elastic strap.

24. The mask of claim 1, wherein said attachment mechanism comprises a behind-head hook-and-loop strap.

25. The mask of claim 1, wherein said attachment mechanism comprises a four point head strap harness.

26. The mask of claim 1, wherein said attachment mechanism comprises a low tack skin adhesive.

27. The mask of claim 1, wherein said attachment mechanism comprises an electron beam cure synthetic polymer adhesive.

28. The mask of claim 1, wherein said molded transparent plastic shield includes a flange extending circumferentially from the perimeter of said molded transparent plastic shield, said flange substantially forming a right angle with the topside of said molded transparent plastic shield.

29. The mask of claim 28, wherein said padding comprises first and second pieces of foam padding which are sandwiched on and affixed to either side of said flange.

30. The mask of claim 28, wherein said padding comprises a single piece of foam padding affixed to the underside of said flange.

31. The mask of claim 29, wherein said attachment mechanism comprises elastic ear loop retainers, each of which passes through said sandwiched foam padding and is affixed to said mold transparent plastic shield.

32. The mask of claim 1, further comprising a warming hood arranged to be coupled to said protective mask and which covers the head, neck and shoulders when so coupled.

33. The mask of claim 32, wherein said warming hood comprises a blanket having an outer layer and an inner layer, said outer and inner layers heat sealed to each other at their respective perimeters, said blanket having at least one access point at which air can be introduced into the blanket between the outer and inner layers, said inner layer comprising a plurality of micro-perforations through which air introduced via said access points is dispersed onto said patient.

34. The mask of claim 33, wherein said outer and inner layers are Mylar sheets.

35. The mask of claim 33, wherein said outer and inner layers are further heat sealed to each other at a plurality of points within the perimeter of said blanket.

36. The mask of claim 35, wherein said plurality of heat sealed points within the perimeter of said blanket form a plurality of linked chambers through which air introduced via said access points is distributed around the interior of said blanket.

37. The mask of claim 33, wherein said warming hood is arranged to be used with a thermal blanket to be used for warming portions of the patient's body other than the head.

38. The mask of claim 37, wherein said thermal blanket has at least one access point at which air can be introduced into the thermal blanket, wherein said warming hood and thermal blanket are arranged to be coupled together such that warm air introduced into the thermal blanket at said at least one access point also flows into the warming hood.

39. The mask of claim 1, wherein said transverse cutout is 4 inches wide by 1 inch high, and said vertical gap is approximately 0.75 inches wide by 3 inches high.

40. The mask of claim 1, wherein said protective mask is provided in various sizes to fit a variety of face sizes.

41. The mask of claim 1, wherein said protective mask is sized to provide a perimeter large enough to protect the entire face without extending beyond the face.

42. The mask of claim 41, wherein said protective mask is provided in small, medium and large sizes, and/or in pediatric and adult sizes.

43. A protective mask suitable for protecting the face of a patient during surgery, comprising:
a molded transparent plastic shield adapted to protect the face of a patient, including the patient's eyes, when said protective mask is installed on the face of said patient, said molded transparent plastic shield having a convex topside and an underside and including:
a transverse cutout through said molded transparent plastic shield capable of providing access to the patient's nose and mouth and arranged to be over the patient's mouth when said protective mask is installed on said patient's face; and
a continuous, pre-cut vertical gap in said transparent plastic shield which runs from said transverse cutout to the lower perimeter of said molded transparent plastic shield;
padding affixed to the perimeter of the underside of said molded transparent plastic shield adapted to contact said patient's face and provides a cushion between said molded transparent plastic shield and said face when said protective mask is installed on the face of said patient, said padding arranged to allow said patient's face to remain substantially visible through said molded transparent plastic shield when said protective mask is installed on the face of said patient; and
an attachment mechanism adapted to secure said protective mask to the face of said patient.
wherein said protective mask is arranged such that, when installed on the face of said patient, said transverse cutout is adapted to be over said patient's mouth and nose, and said continuous, pre-cut vertical gap runs from said transverse cutout to the perimeter of said molded transparent plastic shield over said patient's chin, such that said transverse cutout and said continuous pre-cut vertical gap form a T-shaped opening through said molded transparent plastic shield;
wherein said padding is discontinuous in the area of said continuous pre-cut vertical gap such that, when said continuous pre-cut vertical gap is widened, said padding separates along said discontinuity and said protective mask can be removed from the face of said patient without disturbing any tubing passing through said transverse cutout to said patient's mouth or nose.

* * * * *